US006919566B1

(12) United States Patent
Cadell (10) Patent No.: US 6,919,566 B1
(45) Date of Patent: Jul. 19, 2005

(54) METHOD OF CALIBRATING A SPECTROSCOPIC DEVICE

(75) Inventor: Theodore E. Cadell, Conestogo (CA)

(73) Assignee: NIR Diagnostics Inc., Ontario (CA)

(*) Notice: Subject to any disclaimer, the term of this patent is extended or adjusted under 35 U.S.C. 154(b) by 150 days.

(21) Appl. No.: 10/049,699

(22) PCT Filed: Aug. 31, 2000

(86) PCT No.: PCT/CA00/01005
§ 371 (c)(1),
(2), (4) Date: Jun. 19, 2002

(87) PCT Pub. No.: WO01/16579
PCT Pub. Date: Mar. 8, 2001

Related U.S. Application Data

(60) Provisional application No. 60/151,536, filed on Aug. 31, 1999.

(51) Int. Cl.[7] ............................................. G01N 21/35
(52) U.S. Cl. ........................ 250/339.09; 250/339.07; 250/341.5
(58) Field of Search .................. 250/339.09, 341.5, 250/339.07, 340, 252.1

(56) References Cited

U.S. PATENT DOCUMENTS

| 5,321,265 A | * | 6/1994 | Block ......................... 250/343 |
| 5,362,965 A | | 11/1994 | Maggard |
| 5,576,544 A | | 11/1996 | Rosenthal |
| 5,606,164 A | | 2/1997 | Price et al. |
| 5,680,320 A | | 10/1997 | Helmer et al. |
| 5,945,676 A | * | 8/1999 | Khalil et al. ............ 250/339.12 |
| 6,124,134 A | * | 9/2000 | Stark ........................... 436/63 |
| 6,528,809 B1 | * | 3/2003 | Thomas et al. ............ 250/573 |

FOREIGN PATENT DOCUMENTS

WO          99/34193          7/1999

OTHER PUBLICATIONS

"Strategies for Coupling Digital Filtering with Partial Least–Squares Regression: Application to the Determination of Glucose in Plasma by Fourier Transform Near–Infrared Spectroscopy"; Small, G. et al.; Analytical Chemistry, US, American Chemical Society. Columbus. vol. 65, No. 22; Nov. 15, 1993; pp. 3279–3289.

* cited by examiner

Primary Examiner—David Porta
Assistant Examiner—Faye Polyzos
(74) Attorney, Agent, or Firm—Merchant & Gould P.C.

(57) ABSTRACT

The present invention provides a method of calibrating a spectroscopic device for providing a non-invasive measurement of an analyte level in a sample. The method comprises the steps of: (a) providing a plurality of calibration algorithms; (b) taking a set of non-invasive measurements on said sample with said spectroscopic device; (c) calculating a predicted set of analyte levels for each of the calibration algorithms in response to the set of non-invasive measurements, each of the predicted sets of analyte levels being characterized by a variability range, a slope, an $R_i^2$ (a square of the correlation between said set of non-invasive measurements and said predicted set of analyte levels), and a standard error of prediction; and (d) selecting an appropriate calibration algorithm by using a suitability score based on the variability range, the slope, the $R^2$ an the standard error of prediction for each of the predicted sets of analyte levels. A method of generating suitable calibration algorithms in step (a) is also provided.

10 Claims, 5 Drawing Sheets

Clarke Error Grid

| Zone | % |
|---|---|
| A | 54.11 |
| B | 43.31 |
| C | 0.49 |
| D | 1.96 |
| E | 0.12 |

METHOD OF CALIBRATING A SPECTROSCOPIC DEVICE

FIELD OF THE INVENTION

The present invention relates to the fields of spectroscopy, spectrophotometry, and chemometrics. In particular, the present invention relates to a method of calibrating a spectroscopic device for predicting analyte levels in a non-invasive manner. The method of the present invention is particularly suitable for blood glucose prediction based on near-infrared spectrophotometry measurements.

BACKGROUND OF THE INVENTION

Biotechnological analysis and examination are often based on the measurement of various chemical analytes in the composition of a biological matrix such as blood, interstitial fluid, or living tissue. Such measurements may be used to evaluate a patient's state of health and to determine what, if any, treatment is necessary. For example, the frequent monitoring of blood glucose levels in diabetic persons with glucose meters is often necessary to allow such persons to manage the diabetes mellitus disease, by taking insulin injections or oral drugs to lower blood glucose when required. Intensive treatment based on frequent blood glucose measurements can significantly reduce the incidence of blindness, kidney loss, and other complications associated with diabetes.

Most home-based glucose measurement systems require the patient to invasively collect a blood sample, by pricking his or her finger, placing the sample on an appropriate test strip, and then testing the sample in an optical glucose meter. For millions of diabetics around the world, the use of lancets or other sharp instruments to draw blood for monitoring their insulin levels is a painful process, and one that often builds up calluses on fingers, making the collection of blood even more difficult. This invasive procedure may be especially difficult to perform on children and therefore particularly trying on parents. Furthermore, the test strips required for each blood sample are generally not reusable, and when multiple measurements are taken each day, amount to significant costs from the patient's point of view. Thus, despite the fact that a large number of diabetics should take several measurements throughout each day (for some individuals, physicians recommend testing glucose levels from 4 to 7 times daily), due to the pain, cost, and inconvenience involved, many diabetics do not monitor their glucose levels frequently enough.

Spectroscopy is based on the analysis of how incident radiation interacts with the vibrational and rotational states of molecules which are of analytical interest. Spectroscopic measurement techniques have gained increased popularity because of the ability to provide fast and non-invasive measurements of concentrations of different chemicals or analytes. For the reasons indicated above, this is particularly desirable for home based glucose meters. Spectrophotometry is a type of spectroscopy commonly used to quantitatively measure concentrations of analytes based on spectral energy distribution in the absorption spectrum of a sample solution or medium. In spectrophotometry, the energy distribution is typically analyzed within a range of the visible, ultraviolet, infrared, or near-infrared spectra. For example, near-infrared radiation (NIR) is electromagnetic radiation having a wavelength of between about 0.75 and 2.5 micrometers (i.e. from 150 to 400 THz). Near-infrared spectrophotometry generally uses instruments with quartz prisms in monochromators and with lead sulfide photoconductor cells as detectors to observe absorption bands, and NIR spectrophotometry is increasingly being used to measure in vivo analytes such as glucose, total hemoglobin, albumin cholesterol, and ethanol.

Non-invasive, spectrophotometric measurement of glucose in human beings is performed by focusing an incident radiation source (or sources) on a specific part of the body and detecting the spectral distribution of the radiation transmitted therethrough. The absorbance of light from the incident radiation is due to the chemical components within that body part including water, fat, protein, hemoglobin, melanin, and glucose. One difficulty with glucose measurement spectral analysis, is the spectral overlap between glucose and other chemicals found in blood, often in much greater quantities than glucose. In addition, the thickness, color, and structure of the skin, bones, and blood through which the incident radiation passes will affect the transmission (or reflection/absorption) thereof. Furthermore, the concentration of analytes can vary with changes in activity level, diet, hormone fluctuations, and other factors. Glucose concentration measurements are also particularly susceptible to variations in physical and chemical conditions including temperature, pressure, humidity, and skin hydration. As a result, to perform a reliable non-invasive glucose prediction, NIR spectral measurements should be performed through a vascular equilibrated region of the body, and a NIR glucose spectrophotometer must be carefully designed so that the quality of raw spectral information from an NIR glucose meter is high. See generally Waynant and Chenault, "Overview of Non-Invasive Optical Glucose Monitoring Techniques", IEEE LEOS Newsletter, vol. 12, no. 2 (April 1998); and. Burmeister and Arnold, "Spectroscopic Considerations for Noninvasive Blood Glucose Measurements with Near Infrared Spectroscopy", IEEE LEOS Newsletter, vol. 12, no. 2 (April 1998).

Near-infrared glucose measurements are generally suitable for tissue depths ranging from about 1 mm to 10 cm, and are often performed through a patient's finger tip, although other areas of the body (for example the web between two fingers, an ear lobe, or the upper lip) can also be used. The sample thickness is an important experimental parameter because a greater thickness increases the amount of absorption and thereby lowers the minimum limits for detection, whereas because less incident radiation successfully traverses through a thicker sample (i.e. without being absorbed) effectively increasing the spectral noise: see Burmeister and Arnold, supra.

In addition to the difficulties of obtaining accurate spectral measurements with NIR spectrophotometry, a more significant difficulty associated with such measurements has been the need to calibrate such an instrument so that it may be used by various different individuals, whose analyte concentrations and variability, for example, may differ substantially. Calibration of spectrophotometers (and of analytical instruments in general) is necessary to ensure the accuracy of measurements performed by such devices.

Two approaches to calibrate and predict analyte (e.g. glucose) levels have been used in the prior art. In the first approach, a thorough calibration process is performed separately on each individual with whom the instrument is to be used. This individual calibration process requires taking a number of blood samples over a period of time from the individual, and obtaining reference glucose concentration measurements from these samples. A number of corresponding non-invasive spectroscopic measurements are taken concurrently, and calibration regression analysis is then performed to correlate, e.g. through linear regression analysis, the non-invasive measurements with the reference measurements. In this manner, the spectroscopic device or spectrophotometer is custom calibrated to the specific individual. A major disadvantage of this approach, however, is that the calibration model is limited to data from that particular individual which may have an insufficient amount of information regarding variation of spectra overlapping (interfering with) those of the analyte of interest. It is important to be able to characterize such spectra to enable highly accurate analyte predictions. To alleviate this problem, the custom calibration process may have to be carried out frequently, even on a daily basis.

An alternative calibration approach requires that a universal or general calibration algorithm be developed. This approach is based on the notion that by making a large number of calibration measurements (as in the first approach) a single calibration model that sufficiently accounts for all individual variability of all overlapping or interfering analytes can be calculated. Chemometrics, the application of mathematical, statistical and formal logic methods to chemistry, is generally used to process and compute the spectral intensity data and to produce a calibration model: see Small and Arnold, "Data Handling Issues for Near-Infrared Glucose Measurements", IEEE IEOS Newsletter, vol. 12, no. 2 (April 1998); and Shaffer, Small, and Arnold, "Genetic Algorithm-Based Protocol for Coupling Digital Filtering and Partial Least-Squares Regression; Application to the Near-Infrared Analysis of Glucose in Biological Matrices," Anal. Chem. 68, 2663–2675 (1996). However, for measurements of glucose, and other analytes which vary distinctly and differently from one individual sample to another, a single universal calibration algorithm is often ineffective and can result in significant, and sometimes dangerous, erroneous predictions of analyte concentration levels.

Thus, while NIR measurements provide a non-invasive, fast, painless, and convenient technique to monitor glucose levels, correlation and clinical interpretation of spectral measurements to obtain the true glucose levels is crucial for proper therapy and disease management. Proper calibration of instruments for different patient populations (which will vary in ethnicity, age, weight, and so on) is crucial in obtaining accurate glucose prediction models. Furthermore, careful validation and testing of the non-invasive results and the glucose prediction equation is needed to determine if the glucose correlation is consistent in all clinically important conditions and for all, or at least most, types of patients.

SUMMARY OF THE INVENTION

In a first aspect the present invention provides a method of calibrating a spectroscopic device for providing a non-invasive measurement of an analyte level in a sample, comprising:

(a) providing a plurality of calibration algorithms;

(b) taking a set of non-invasive measurements on said sample with said spectroscopic device;

(c) calculating a predicted set of analyte levels for each of the calibration algorithms in response to the set of non-invasive measurements, each of the predicted sets of analyte levels being characterized by a variability range, a slope, an $R^2$ (a square of the correlation between said set of non-invasive measurements and said predicted set of analyte levels), and a standard error of prediction; and (d) selecting an appropriate calibration algorithm by using a suitability score based on the variability range, the slope, the $R^2$ and the standard error of prediction for each of the predicted sets of analyte levels.

Preferably, step (d) comprises a method according to claim 1 wherein, step (d) comprises (i) selecting the predicted sets of analyte levels in which the standard error of prediction is less than an upper error limit, the variability range is greater than a lower range limit, and the slope is between a lower slope limit and an upper slope limit said lower and upper slope limits defining an acceptable slope range;

(ii) for each of the predicted sets selected in step (i), calculating a suitability score in response to the slope, the $R^2$ and the standard error of prediction for that predicted set, and selecting the calibration algorithm corresponding to the predicted set having the optimal (highest) suitability score as the appropriate calibration algorithm;

(iii) if no predicted sets are selected in step (i), selecting the predicted sets of analyte levels in which the variability range is lower than the lower range limit and in which the standard error of prediction is less than the upper error limit, (iv) from each of the predicted sets selected in step (iii), selecting the calibration algorithm corresponding to the predicted set having the lowest standard error of prediction as the appropriate calibration algorithm; and (v) if no predicted sets are selected in step (i), or step (iii), determining that no calibration algorithm is appropriate.

Also preferably, the acceptable slope range may be subdivided into a plurality of subranges corresponding to a plurality of levels, comprising a first level and one or more subsequent levels, and if no predicted sets are selected in the first level, then repeating step (i) at each subsequent level until a predicted set is selected or there are no more subsequent levels.

Preferably, the plurality of calibration algorithms provided in step (a) are first generated by the steps of (i) compiling non-invasive and corresponding reference data sets of measurements of analyte levels for each of a number of samples;

(ii) rejecting data sets that are not suitable for calibration;

(iii) combining data sets that are suitable for calibration into a plurality of groups depending on whether correlations of the combined data sets meet predetermined criteria; and (iv) generating a calibration algorithm for each of the groups of data sets.

Steps (a), (c), and (d) of the method of the present invention may be performed on a computer associated with the spectroscopic device. Furthermore, the sample may be an individual patient, the spectroscopic device may be a near-infrared spectrophotometer, and the analyte may be selected from the group consisting of glucose, hemoglobin, albumin, cholesterol, and ethanol.

The objects and advantages of the present invention will be better understood and more readily apparent with reference to the remainder of the description in conjunction with the accompanying drawings.

BRIEF DESCRIPTION OF THE DRAWINGS

In the drawings which illustrate, by way of example, a preferred embodiment of the invention.

DETAILED DESCRIPTION OF THE INVENTION

As mentioned, the present invention relates to a method of calibrating a spectroscopic device for predicting analyte levels in a non-invasive manner. The present invention can be used with a typical NIR spectrophotometer system having a light source which is projected through the item to be examined, a sample interface mechanism, a spectrometer to separate the light into its component wavelengths, a detector, amplification electronics and a computer. By measuring the loss (absorption), between the source and the detector and applying appropriate chemometric (mathematical) techniques, it is possible to non-invasively determine the chemicals being examined since different chemicals absorb different amounts of light at different wavelengths. Such a spectrophotometric device and method are described in detail in U.S. Pat. No. 5,361,758, the contents of which are incorporated herein by virtue of this reference. While the present description relates primarily to glucose measurement, one of the major fields of application for NIR measurement at present, it will be understood that the principles of the present invention equivalently apply to other analytes non-invasively measured using various spectroscopic techniques.

To utilize the NIR spectrum for glucose measurement, it is necessary to use a spectrometer which has wide dynamic range, a high signal to noise ratio, and exhibits low scattering losses. The output from the spectrometer is used to generate spectra with high precision both in absorbance and wavelength. Significant glucose absorption bands are centered about wavelengths of 1.67, 2.13, 2.27, and 2.33 micrometers (as discussed in Small and Arnold, "Data handling Issues for Near-Infrared Glucose Measurements", supra). In addition to these wavelengths there are significant glucose absorption bands at 0.97 and 1.12 micrometers which wavelengths allow transmission measurement through a greater distance in the tissue. To be able to use NIR to measure a particular compound/analyte, chemometric mathematical analysis is applied to the measured spectrum. The mathematical analysis techniques are carried out by a computer equipped with advanced software capable of interpreting the resulting complex spectra.

To universally calibrate an NIR spectrophotometer, the absorbance associated with the compound or analyte of interest must first be measured on a relatively large number of samples. These NIR measurements are then compared to measurements made in a more traditional and more accurate invasive manner. From these comparisons an algorithm is developed that characterizes the analyte to be measured. The methods used to generate calibration models for NIR spectrophotometers are sophisticated. An important criterion is that calibration samples be uncorrelated with other chemical species concentrations. Satisfaction of these criteria is burdensome because of the large number of chemical species typically present in a biological matrix or growth medium.

The present invention provides a multi-algorithm calibration method for use with a spectroscopic device capable of predicting analyte levels in a biological matrix, such as blood glucose levels, for a variety of different samples with significantly greater accuracy than prior art universal single calibration models. The calibration method of the invention has two key parts: the generation of a plurality of different algorithms and the selection of the algorithm which is most appropriate for generating an accurate prediction of analyte concentration.

To generate suitable calibration algorithms, the non-invasive and reference measurement data sets for a number of individuals are first compiled. Once this is achieved, correlation techniques are carried out to relate non-invasive spectral measurements to reference glucose levels. At this stage the suitability of individual data samples for calibration purposes must be considered. If some of the non-invasive spectral measurements in a data set result in a saturation of the measurement equipment, e.g. at the output of an analog-to-digital converter, then the data sample should be disqualified for use in a calibration algorithm. Similarly, if the range of variability of the non-invasive spectral measurements in a data set is too small, the data sample should also be disqualified from calibration. Furthermore, if the correlation of glucose in a particular data set is undesirably correlated to another variable, such as the concentration of another chemical, the sample should again be disqualified. As a result, a large numbers of sample sets will not be suitable for calibration algorithm development.

The grouping or combining of calibration-suitable data sets (each specific to a particular individual) into different algorithms occurs on a trial and error basis, by repeatedly combining these data sets and performing a new correlation on the combined sets of data. If the correlations of the combined sets meet certain criteria, then the combination is acceptable, if not, a different combination is attempted. Once a combination is deemed acceptable, the addition of a further data set is attempted and its acceptability is determined in turn. In this manner, a combination of data sets for an algorithm grows from 2 data sets, to 3 data sets, to 4 data sets, and so on until a sufficiently large number of data sets is obtained from which a reliable calibration algorithm can be developed.

In combining data sets for a single algorithm, two criteria are key. First, any correlation of glucose in the combined data set group with other parameters must be minimized. Such undesirable correlations may be exhibited with different chemical species concentrations or other time varying quantities. A suitable quantitative test for this criteria is to ensure that all undesirable correlations of the combined data sets, as indicated by the square of the correlation coefficient $R_u^2$ (for the undesirable correlations), are less than a certain limit, such as $R_u^2 < 0.10$. In known manner, the correlation coefficient, $R_u$, is a measure of the tendency of two variables to vary together. If the addition of a data set to another data set or to a suitable sub-combination of data sets does not satisfy this criteria, the new combination will not be acceptable.

In addition, the combination of data sets can be optimized by ensuring that the data sets exhibit a high degree of correlation with one another, so a second criteria in combining data sets should require that the data sets in a particular group be sufficiently correlated with one another, This can be achieved, for example, by ensuring that the Standard Error of Prediction (SEP) is minimal and the square of the correlation coefficient, $R^2$, together with the slope relating reference glucose to predicted glucose, are greater than about 0.8 for an existing sub-combination of data sets and another data set being potentially combined with that sub-combination.

In an alternate embodiment of the present invention, instead of successively adding on to, or building up, groups of data sets for a calibration algorithm, a large group of calibration suitable data sets can be initially taken up at random. In this embodiment, data sets are removed from the group, and the SEP and correlation criteria above are reevaluated. If the SEP, slope and correlation criteria improve after the removal of the data set, the data set is permanently removed from the group, whereas if the criteria do not improve, the data set is reinstated back into the group. Using this top-down approach, the removal of data sets can cease when the criteria meet acceptable limits.

The SEP, slope, and correlation calculations for determination of the calibration algorithm groupings (and the associated calibration algorithms) become increasingly complex with increasing amounts of data and are preferably carried out using partial least-squares (PLS) regression analysis. The PLS analysis techniques are well known to those skilled in the art and provide good linear approximation by removing considerable redundant information: see generally Small and Arnold, "Data handling Issues for Near-Infrared Glucose Measurements", supra. Other types of analysis, such as partial component analysis (PCA) or artificial neural networks (ANN), can also be used.

This calibration algorithm generation process is used to generate at least two groups of data sets (corresponding to groups of individuals), each providing a calibration model or algorithm for predicting the level of analyte present in a biological matrix based on a non-invasive spectroscopic measurement. Preferably, two initial groups of data set are developed, and, from these two groups, additional groups can be generated. These additional groups are generally smaller in size than the two initial groups and may meet more stringent correlation criteria. These additional groups may be constructed with the top-down approach described above, wherein data sets are selectively removed from an initial group to determine if the correlation criteria improve or deteriorate after the removal.

Given the availability of multiple calibration algorithms, it is necessary to select the most suitable of these algorithms for predicting the levels of analyte in any given patient or sample. Once this is done the spectroscopic device is calibrated with the selected algorithm. The algorithm selection process is generally independent of the process used to generate the multiple algorithms, although it will clearly depend on the number of different algorithms that are available.

For any given patient or sample on which the non-invasive spectroscopic measurement is to be made, it is necessary first to compile a set of highly accurate reference measurements and corresponding non-invasive spectral measurements at selected intervals over a period of time. In a preferred embodiment, two successive non-invasive spectral measurements are successively taken each measurement interval, and their mean is then taken as a single non-invasive measurement for that interval.

Before algorithm selection begins, two variables may be set to determine the stringency of acceptance requirements for patients (i.e. whether at least one of the available calibration algorithms will be found suitable for a patient). These are (i) a lower range limit for the range of glucose or analyte variability in the data set (if the data does not vary significantly it may not provide sufficient information to be useful), and (ii) an upper error limit ($SEP_{max}$) for the standard error of prediction (SEP), i.e. the square root of the mean of the squared deviations of the reference analyte concentrations from the analyte concentration values predicted by a calibration algorithm.

From the non-invasive spectral measurements, a predicted set of analyte concentration levels are calculated according to each calibration algorithm. When compared to the reference set of concentration levels, each predicted set will be calculated from a linear regression or "best fit" line characterized by: a range of glucose level variability; a slope (which ideally equals 1, i.e. the predicted values correspond directly to the reference values); a correlation coefficient R, defining the correlation of the predicted value set with the reference value set; and a standard error of prediction (SEP), as defined above. Note that as the correlation coefficient R increases the SEP will decrease, and vice versa, except in cases in which there is an offset or bias in the predicted analyte.

By way of example, and not to restrict the scope of the present invention, the algorithm selection process can include 4 levels or steps. In a first level, if the predicted data set for an algorithm meets the following criteria i) SEP<upper error limit ($SEP_{max}$)

ii) Analyte range>lower range limit and iii) 0.5<slope (of regression line)<1.05, a suitability score is calculated according to the following equation:

$$score = (slope)(R^2)/(SEP)$$

If more than one algorithm meets the first level criteria, the algorithm with the highest suitability score is selected and the selection process is complete. If no algorithm qualifies in terms of the first level criteria, the selection process advances to a second level.

The second level is identical to the first level except that the slope criteria becomes $$0.33 < slope \text{ (of regression line)} < 0.5$$

For algorithms that meet this revised slope criterion (and the SEP and range criteria), a suitability score is calculated as in the first level. Again, if more than one algorithm qualifies at the second level, the algorithm with the highest score is selected, and the selection process is complete.

At a third level, if none of the algorithms qualify at either the first level or the second level and the range of analyte measurements is greater than the lower range limit, the sample or patient is excluded from measurement, since under these circumstances no calibration algorithm can be relied on to perform accurately.

Lastly, at a fourth level, if none of the algorithms qualify at either the first level or the second level and the range of analyte measurements is lower than the lower range limit, the algorithm with the lowest SEP is selected if that SEP is less than the upper error limit. If the SEP is greater than the upper error limit, the patient is again excluded from measurement. Thus, in the fourth level, the SEP becomes the sole factor in deciding whether an algorithm should be accepted.

Note that the slope criteria limits in the first and second levels described above are preferred limits, and these levels can also be varied somewhat (similar to the lower range limit and upper error limit) depending on the application and acceptance requirements. Also, the number of levels or steps used in the algorithm selection process can vary, from a single level covering the entire preferred range, to two or more levels subdividing the preferred range into two or more range limits or range criterion. Regardless of the number of levels, however, the third and fourth levels as described above will correspond to the last two levels, in which the patient is either excluded, or a decision to accept an algorithm is made on the basis of SEP alone. It will be readily appreciated by those skilled in the art that the number of levels or steps chosen is a matter of preference only.

To illustrate the principals of the present invention, the multiple algorithm calibration method was used to calibrate a NIR spectrophotometer for measuring glucose levels in a number of different patients. All reference data measurements were taken with a glucose analyzer such as the industry standard YSI™ (Yellow Springs Instruments) Glucose Analyzer which provides precise glucose measurements on (invasive) blood samples. The inventor found that only approximately 6% of single NIR patient data sets qualified for calibration purposes, given the criteria described above. These calibration qualified sets of data were grouped into two initial calibration algorithm sets, each initial group was built up to a group with 33 sets of data within it. Eleven additional groups were spun off from these two initial groups and each of these groups had at least 8 sets of data within it. Thus, thirteen different calibration algorithms were available for predicting glucose levels.

The algorithm selection was based on a total of 24 reference measurements (ie. YSI™ measured) and 24 means of two NIR finger measurements, taken from a patient over a three day period. The above described algorithm selection process was run for a number of different patients (not involved in the calibration process).

Figure 1:
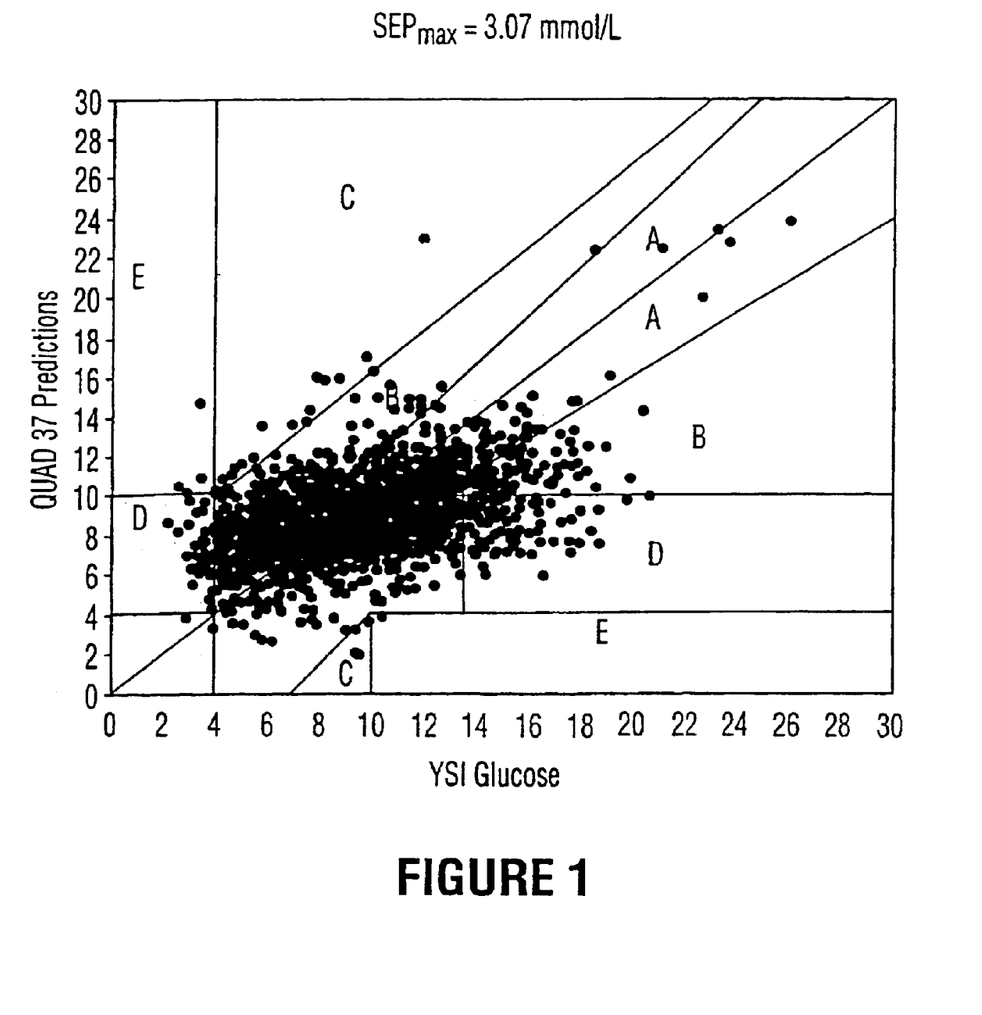
FIG. 1 is a correlation scatterplot of glucose predictions for a number of different patients based on a universal, single calibration model.

FIG. 1 shows a correlation scatterplot of glucose predictions for a number of different patients based on a universal calibration model (QUAD 37). The scatterplot in FIG. 1 is superimposed on a Clarke error grid, as described in Clarke and Cox, "Error Grid Analysis", Diabetes Care, 10:622–628 (1987). The Clarke error grid breaks the correlation space into five regions (A–E) that assess measurement accuracy on the basis of validity of the corresponding clinical decision Correlation points falling within the "A" region correspond to the correct clinical decision being made based on the similarity between the actual and predicted glucose levels. (i.e. the predicted values deviate by no more than 20% from the reference values). In the "B" region, the predicted values deviate by more than 20% from the reference values, but treatment decisions made based on the predicted levels of glucose would not jeopardize or adversely affect the patient. In regions "C", "D", and "E", the predictions significantly deviate from the reference values, and treatment decisions based on these predictions may well be harmful to a patient. The Clarke error grid is often used to evaluate the clinical consequences of home-use blood glucose monitor errors, in contrast to more conventional anal methods which may be more suitable for laboratory reference devices.

Figure 2:
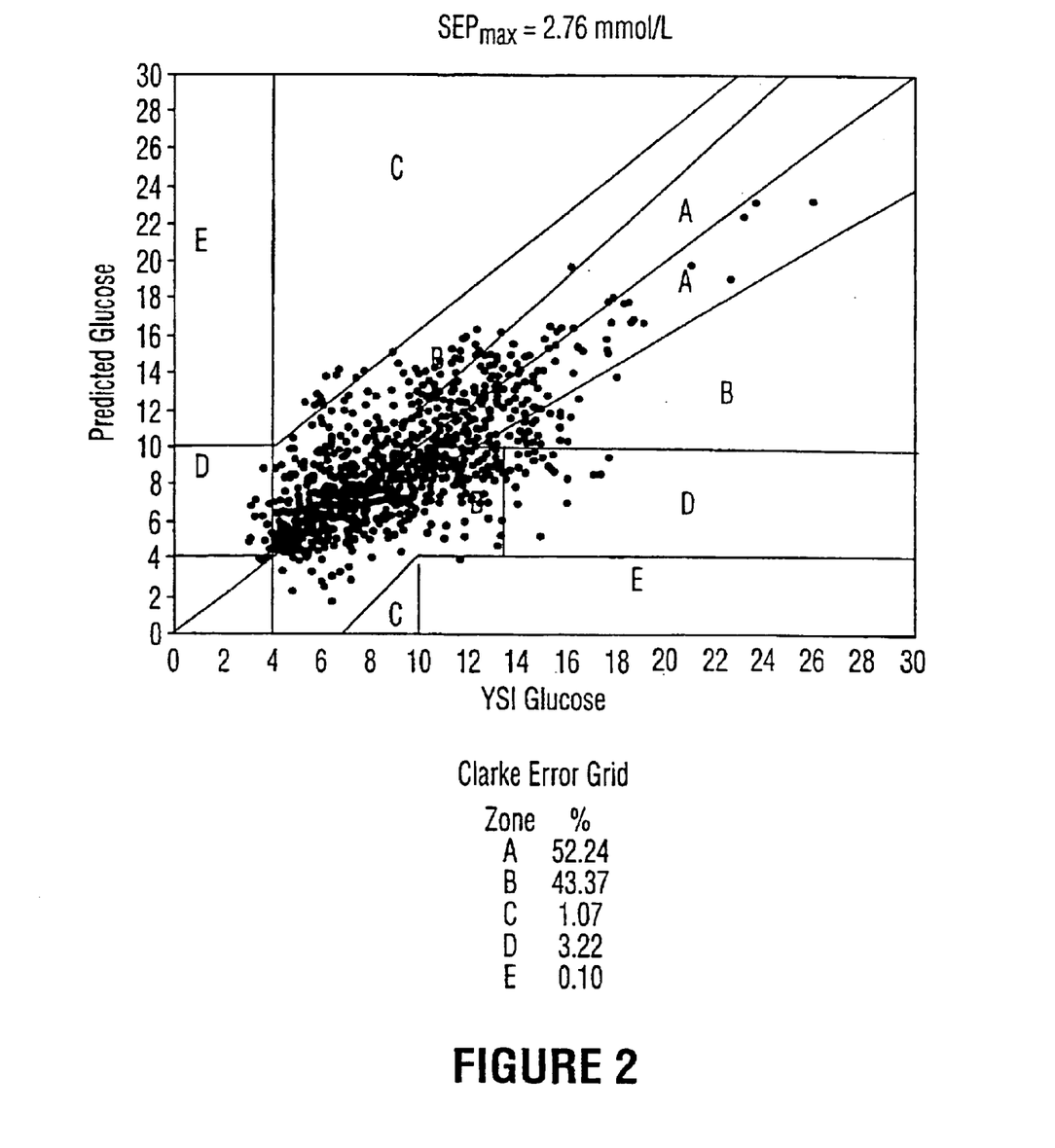
FIG. 2 is a correlation scatterplot of glucose predictions for a number of patients based on the multiple algorithm calibration model according to the present invention.
Figure 3:
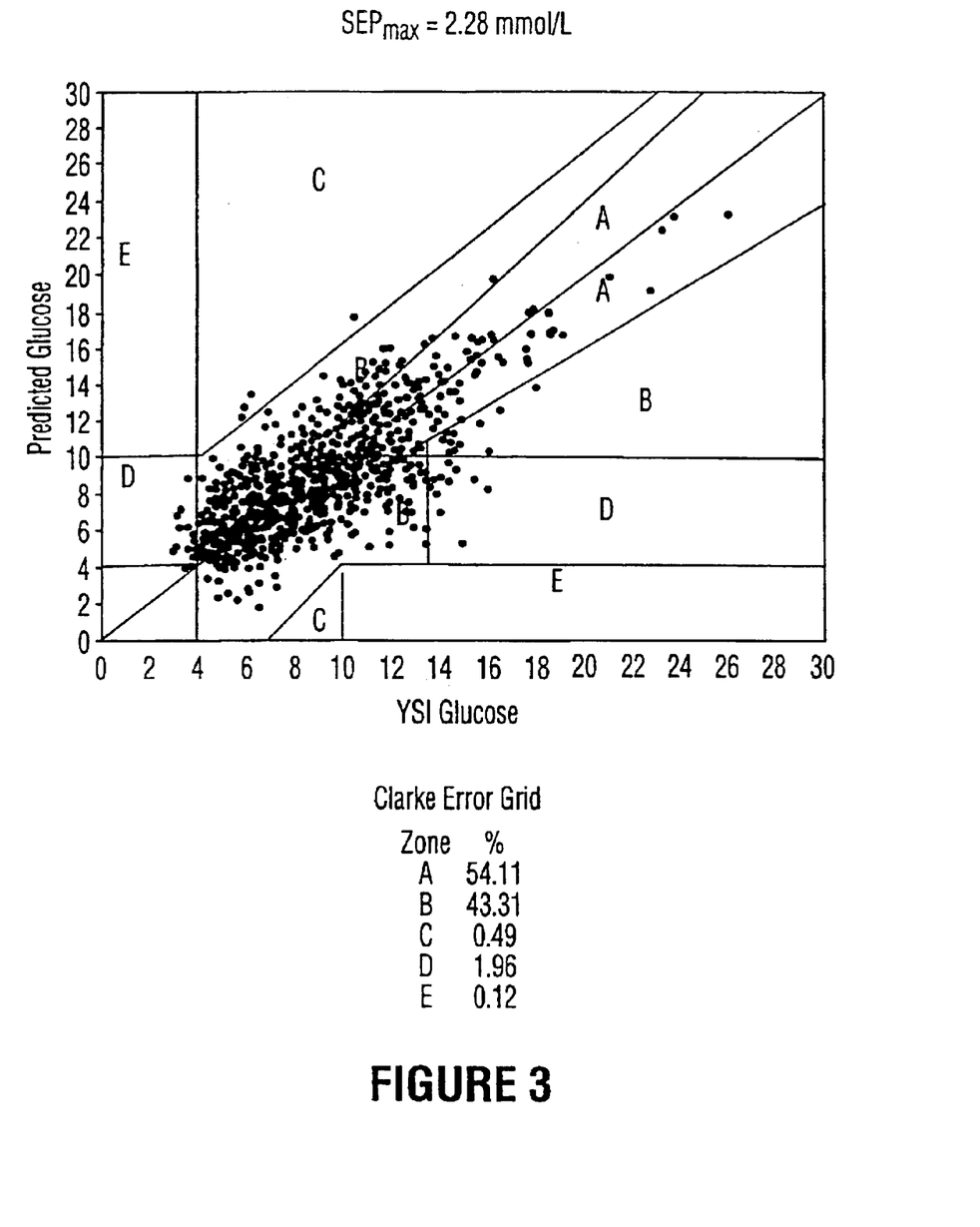
FIG. 3 is another correlation scatterplot of glucose predictions for a number of patients based on the multiple algorithm calibration model according to the present invention.

Referring to FIG. 1, it can be seen that the upper error limit $SEP_{max}$ for this universal calibration algorithm is 3.07 mmol/L and that significant amounts of the data are outside acceptable limits or regions. In contrast, FIG. 2 shows the correlation scatterplot of glucose predictions for 25 patients based on the multiple algorithm calibration model according to the present invention, with $SEP_{max}$ equal to 2.76 mmol/L. Similarly, FIG. 3 shows a correlation scatterplot of glucose predictions for 22 patients based on the multiple algorithm calibration model according to the present invention, with $SEP_{max}$ equal to 2.28 mmol/L. Both the predictions in FIG. 2 and particularly FIG. 3 exhibit much better accuracy than those in FIG. 1 (calibrated according to a universal algorithm).

Figure 4:
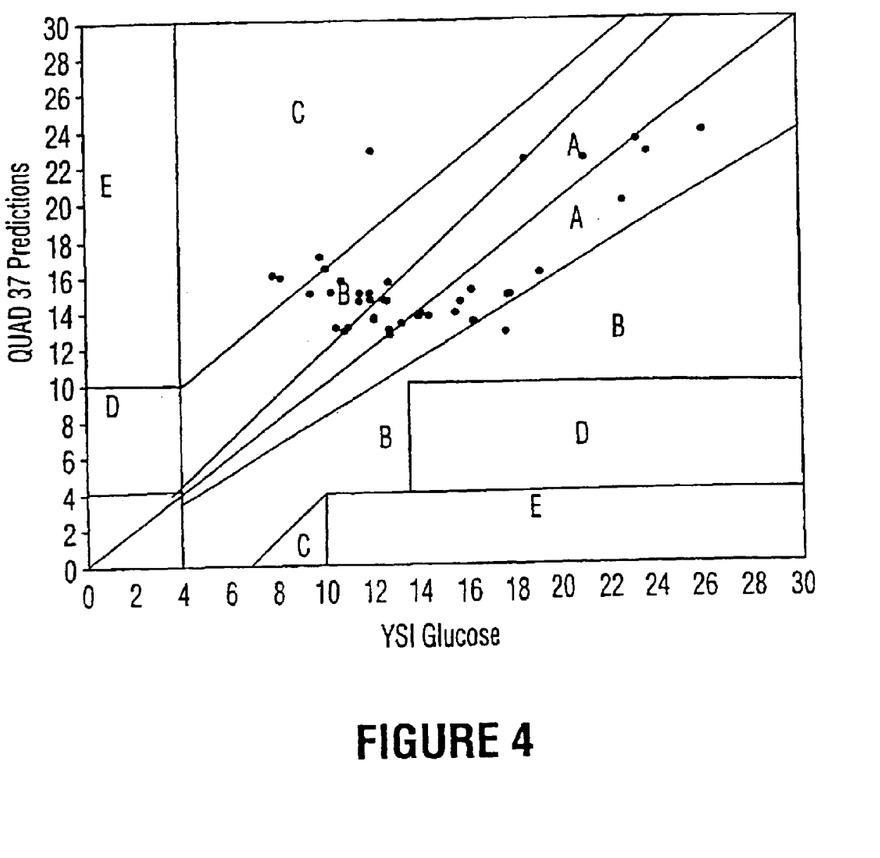
FIG. 4 is a correlation scatterplot of glucose predictions for a typical patient based on a universal, single calibration model.
Figure 5:
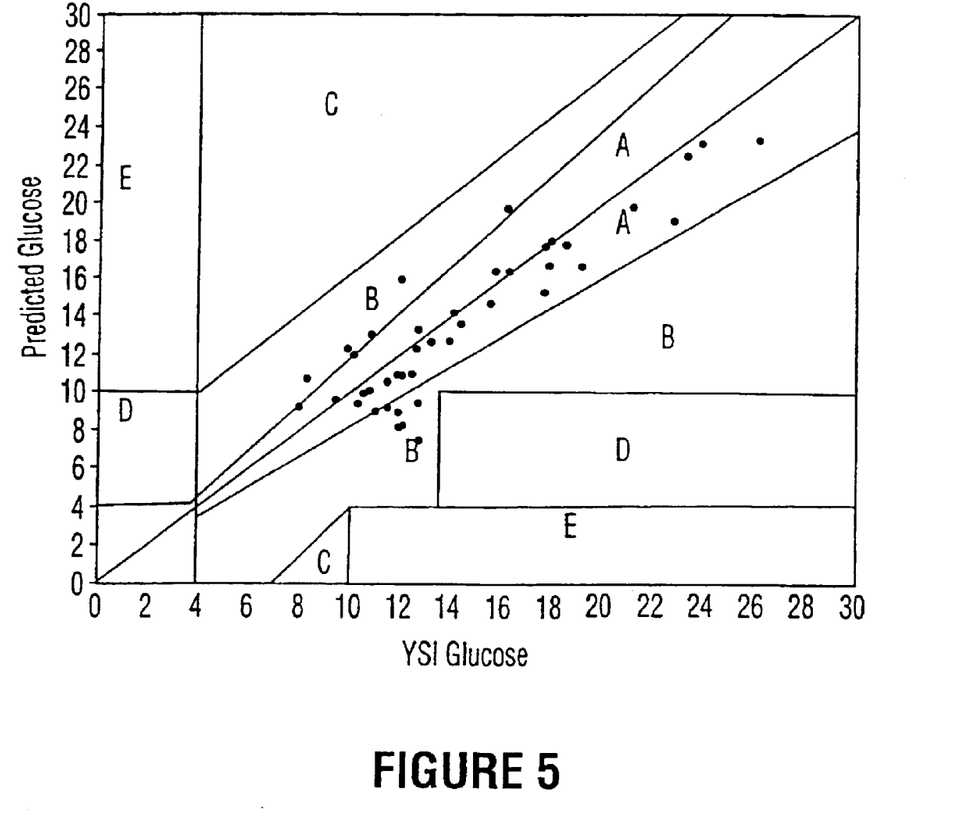
FIG. 5 is a correlation scatterplot of glucose predictions for the same typical patient based on the multiple algorithm calibration model according to the present invention.

Similarly, FIG. 4 shows a set of correlation data for a typical patient, calibrated according to the same universal algorithm, whereas FIG. 5 shows the correlation data for the identical patient calibrated according to the multiple algorithm method of the present invention. Once more, the improved accuracy of the glucose predictions based on the calibration method of the present invention is evident.

It will be clear to those skilled in the art that the principles of the present invention are applicable to a broad range of spectroscopic applications. For example, NIR radiation can be used to penetrate such items as human tissue, vials of blood, or containers of milk—all normally considered opaque. Mathematical analysis of the resulting absorption spectrum determines the composition of the substance penetrated by the light. Thus, in a blood testing lab, samples can be examined without contact by passing the light through a plastic vial containing the liquid. Similarly, in a dairy application, the NIR light is passed through a bag of milk and such parameters as butterfat, solid particles and lactate are measured. The multiple algorithm method of the present invention is easily extendible to these types of non-invasive measurements as well. Furthermore, the method of the present invention can also be applied to the non invasive measurement of a number of other blood analytes such as cholesterol, hemoglobin, Hb1Ac, Fructosine, and 1.5 AG.

While preferred embodiments of the present invention have been described, the embodiments disclosed are illustrative and not restrictive, and the invention is intended to be defined by the appended claims.

I claim:

1. A method of calibrating a spectroscopic device for providing a non-invasive measurement of an analyte level in a sample, comprising:
   (a) providing a plurality of calibration algorithms;
   (b) taking a set of non-invasive measurements on said sample with said spectroscopic device;
   (c) calculating a predicted set of analyte levels for each of the calibration algorithms in response to the set of non-invasive measurements, each of the predicted sets of analyte levels being characterized by a variability range, a slope, an $R^2$ (a square of the correlation coefficient between a reference value set and said predicted set of analyte levels), and a standard error of prediction; and
   (d) selecting an appropriate calibration algorithm comprising the steps selected from the group consisting of:
      (1) calculating a suitability score according to the slope, the $R^2$ and the standard error of prediction for said predicted set;
      (2) selecting the calibration algorithm corresponding to said predicted set having the highest suitability score as the appropriate calibration algorithm;
      wherein in said predicted sets of analyte levels the standard error of prediction is less than an upper error limit, wherein the variability range is greater than a lower range limit, and wherein the slope is between a lower slope limit and an upper slope limit, said lower and upper slope limits defining an acceptable slope range; and
      (3) selecting the calibration algorithm corresponding to the predicted set having the lowest standard error of prediction as the appropriate calibration algorithm: wherein in said predicted sets of analyte levels, the variability range is lower than the lower range limit and wherein the standard error of prediction is less than the upper error limit;

(e) declaring that no calibration algorithm is appropriate if no calibration algorithm is selected in step (d)(1), or step (d)(2).

2. A method according to claim 1 wherein, said acceptable slope range is subdivided into a plurality of subranges corresponding to a plurality of levels, comprising a first level and one or more subsequent levels, and if no predicted sets are selected in the first level, then repeating step (d)(1) at each subsequent level until a predicted set is selected or there are no more subsequent levels.

3. A method according to claim 2, wherein, said acceptable slope range is defined by a lower slope limit of about 0.3 an upper slope limit of about 1.05.

4. A method according to claim 1 wherein, said lower slope limit is less than one and said upper slope limit is greater than one.

5. A method according to claim 4 wherein, said lower slope limit is about 0.3 and said upper slope limit is about 1.05.

6. A method according to claim 1 wherein, the plurality of calibration algorithms provided in step (a) are first generated by the steps of:

(i) compiling non-invasive and corresponding reference data sets of measurements of analyte levels for each of a number of samples;

(ii) rejecting data sets that are not suitable for calibration;

(iii) combining data sets that are suitable for calibration into a plurality of groups depending on whether correlations of the combined data sets meet predetermined criteria; and (iv) generating a calibration algorithm for each of the groups of data sets.

7. A method according to claim 6 wherein the predetermined criteria in step (iii) include minimizing correlations of the combined data sets in a particular group with parameters other than said analyte and maximizing the correlation between data sets in a particular group.

8. A method according to claim 6 wherein steps (iii) and (iv) are performed using partial least-squares regression analysis.

9. A method according to claim 6 wherein steps (a), (c), and (d) are performed on a computer associated with the spectroscopic device.

10. A method according to claim 1, wherein the sample is an individual patient, the spectroscopic device is a near-infrared spectrophotometer, and the analyte is selected from the group consisting of glucose, hemoglobin, albumin, cholesterol, and ethanol.

* * * * *